United States Patent
Eversull et al.

(10) Patent No.: US 11,260,200 B1
(45) Date of Patent: Mar. 1, 2022

(54) CATHETERS AND METHODS FOR MAKING THEM

(71) Applicant: CLPH, LLC, Palo Alto, CA (US)

(72) Inventors: Christian S. Eversull, Palo Alto, CA (US); Stephen A. Leefleng, Sunnyvale, CA (US)

(*) Notice: Subject to any disclaimer, the term of this patent is extended or adjusted under 35 U.S.C. 154(b) by 289 days.

(21) Appl. No.: 16/132,441

(22) Filed: Sep. 16, 2018

Related U.S. Application Data (60) Provisional application No. 62/558,989, filed on Sep. 15, 2017.

(51) Int. Cl.
| | |
|---|---|
| *A61F 2/95* | (2013.01) |
| *A61M 25/00* | (2006.01) |
| *B29D 23/00* | (2006.01) |
| B29K 27/18 | (2006.01) |
| A61B 17/34 | (2006.01) |

(52) U.S. Cl.
CPC ........... *A61M 25/0009* (2013.01); *A61F 2/95* (2013.01); *A61M 25/0045* (2013.01); *B29D 23/00* (2013.01); *A61B 17/3468* (2013.01); *A61F 2/9517* (2020.05); *B29K 2027/18* (2013.01)

(58) Field of Classification Search
CPC . A61M 25/0009; A61M 25/0045; A61F 2/95; B29D 23/00
See application file for complete search history.

(56) References Cited

U.S. PATENT DOCUMENTS

| | | | | |
|---|---|---|---|---|
| 5,246,430 | A * | 9/1993 | MacFarlane | A61B 17/22031 600/435 |
| 9,480,589 | B2 * | 11/2016 | Breyer | A61F 2/966 |
| 2012/0123327 | A1 * | 5/2012 | Miller | A61M 25/0012 604/95.04 |
| 2015/0216692 | A1 * | 8/2015 | Shannon | B32B 38/06 623/1.12 |
| 2015/0273181 | A1 * | 10/2015 | Leeflang | A61B 5/6852 600/373 |
| 2016/0325074 | A1 * | 11/2016 | Lareau | A61M 25/0029 |

* cited by examiner

*Primary Examiner* — Jeffry H Aftergut
*Assistant Examiner* — Jaeyun Lee
(74) *Attorney, Agent, or Firm* — William A. English; Vista IP Law Group LLP (57) ABSTRACT

Apparatus and methods are provided for making catheters having relatively larger distal and proximal regions and/or including intermediate layers that minimize or eliminate gaps during manufacturing, and to catheters or other tubular devices made using such apparatus and methods.

17 Claims, 5 Drawing Sheets

CATHETERS AND METHODS FOR MAKING THEM

RELATED APPLICATION DATA

This application claims benefit of provisional application Ser. No. 62/558,989, filed Sep. 15, 2017, the entire disclosure of which is expressly incorporated by reference herein.

FIELD OF THE INVENTION

The present invention relates generally to apparatus and methods for making catheters, sheaths, or other tubular devices, and, more particularly, to apparatus and methods for making tubular devices including intermediate layers and/or having relatively large proximal and/or distal ends.

BACKGROUND

Catheters are elongate tubular devices sized for introduction into body passages and cavities of a patient, such as a patient's vascular system, gastrointestinal system, abdominal cavity, and the like. A catheter may include one or more lumens intended for passing various other devices, prostheses, agents, and/or fluids into a body lumen or cavity accessed by the catheter. Catheters are often used to traverse tortuous anatomy and/or perform diagnostic or interventional procedures within the body. To perform these functions, catheters often must possess complex functional and mechanical properties. Catheters are often constructed of multiple layers and/or segments in order to achieve desired properties. For example, catheters often comprise an inner layer or liner, a reinforcing layer, such as a metallic coil or braid and an outer layer or jacket. Using conventional methods of construction, adding multiple layers, including intermediate layers may lead to sink, air bubbles, wall thickness irregularities, and/or other undesirable results. Thus, improved devices and methods relating to intermediate catheter layers are needed.

In addition, catheter devices are increasingly utilized to deploy large devices within the body. This requires a large lumen or luminal segment to accommodate the large device. In some cases the largest segment can be limited to the distal portion of the device and the patient may benefit from a smaller intermediate segment of the device, e.g. to safely track through the vasculature and/or minimize trauma to at the point of entry. Further deployment of such large devices may require high forces to be applied to the catheter.

Thus, catheter designs to accommodate such large device, minimize trauma or maximize patient safety may are needed.

SUMMARY

The present invention is directed to catheters, sheaths, or other tubular devices including multiple layers or segments. More particularly, the present invention is directed to tubular devices having relatively large proximal and/or distal ends and methods for making such tubular devices.

In one embodiment, a method is provided for making a tubular device including relatively large proximal and distal ends that includes providing a mandrel including a proximal segment having a first diameter, an intermediate segment extending from the proximal segment having a second diameter, and a distal segment having a third diameter extending from the intermediate segment opposite the proximal segment, the second diameter being smaller than the first and third diameters. A liner is applied around the mandrel between the distal, intermediate, and proximal segments, a reinforcement layer is directed around the liner over at least a portion of the mandrel, and an outer jacket is directed over the reinforcement layer and the liner between the distal, intermediate, and proximal segments. The mandrel is then removed to provide a tubular body comprising a primary lumen defining a proximal region corresponding to the proximal segment, an intermediate region corresponding to the intermediate segment, and a distal region corresponding to the distal segment of the mandrel.

In another embodiment, an apparatus for performing a medical procedure is provided that includes a tubular body comprising a proximal region, an intermediate region extending from the proximal region, and a distal region extending from the intermediate region, the tubular body comprising a primary lumen extending through the proximal, intermediate, and distal regions, the primary lumen having an intermediate diameter in the intermediate region that is smaller than a proximal diameter in the proximal region and a distal diameter in the distal region; a handle attached to the tubular body such that the proximal region is contained within the handle and the intermediate region extends from the handle; a deployable device disposed within the primary lumen within the distal region; and an actuator for deploying the deployable device from the distal region.

In still another embodiment, a method is provided for making a tubular device that includes providing a mandrel including a first segment having a first diameter, a second segment having a second diameter smaller than the first diameter, and a transition segment tapering from the first segment to the second segment; providing a strip of material having a first length having a first thickness and a second length having a second thickness greater than the first thickness; helically wrapping the strip around the mandrel such that the first length wraps around the first segment and the second length wraps around at least a portion of the second segment to provide a liner having a substantially uniform outer diameter over the first segment, transition segment, and the at least a portion of the second segment; directing a reinforcement layer around the liner over at least a portion of the mandrel; directing an outer jacket over the reinforcement layer and the liner between the distal, intermediate, and proximal segments; and removing the mandrel to provide a tubular body comprising a primary lumen defining a first region corresponding to the first segment, and a second region corresponding to the second segment of the mandrel.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
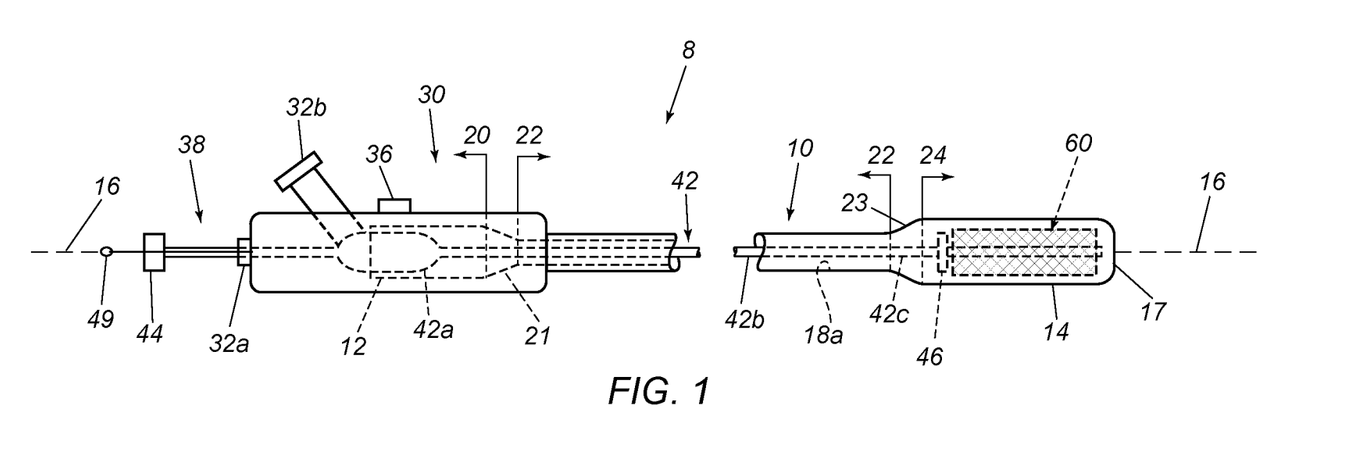
FIG. 1 is a side view of an exemplary embodiment of a catheter including an enlarged distal region.
Figure 2:
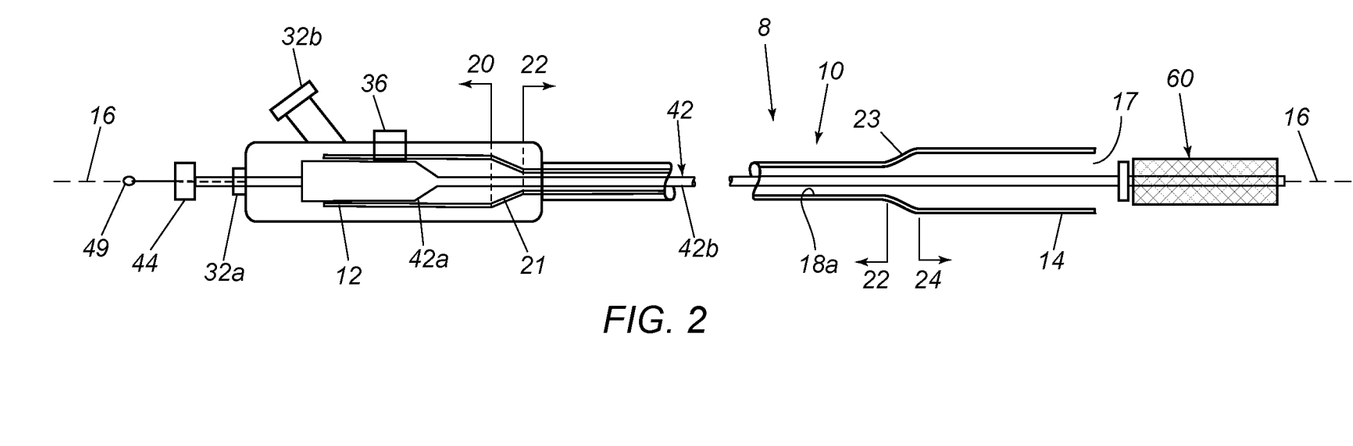
FIG. 2 is a longitudinal cross-sectional view of the catheter of FIG. 1 showing a manifold and deployable device.

Turning to the drawings, FIGS. 1 and 2 show an apparatus 8 designed for accessing a body lumen or cavity, e.g., to perform a diagnostic, therapeutic, and/or other medical procedure within a patient's body. In exemplary embodiments, the apparatus 8 may be a prosthesis delivery catheter, a guide catheter, a sheath, a procedure catheter, an imaging catheter, an ablation and/or mapping catheter, a balloon catheter, a circulatory support catheter, or other tubular device sized for introduction into a body lumen, such as a vessel within a patient's vasculature, a passage within a patient's gastrointestinal tract, urogenital tract, reproductive tract, respiratory tract, lymphatic system, and the like (not shown).

Generally, the apparatus 8 includes a tubular body 10 including a proximal end 12, a distal end 14 sized for introduction into the patient's body, and one or more lumens 18 extending between the proximal and distal ends 12, 14, thereby defining a central longitudinal axis 16. In addition, the apparatus includes a handle or hub 30 on the proximal end 12, and a deployable and/or expandable device 60 carried within the distal end 14. The tubular body 10 may include one or more lumens and may be constructed of one or more layers (e.g., layered radially) and/or segments (e.g., segmented axially), typically being constructed of multiple layers and multiple segments to impart multiple desired properties throughout the tubular body 10, as described further elsewhere herein.

For example, as shown in FIG. 2, the tubular body 10 includes a proximal region 20, e.g., within the handle 30, an intermediate region 22 extending from the handle 30, and a distal region 24 carrying the deployable and/or expandable device 60. The intermediate region 22 has an outer diameter, inner diameter, or other cross-sectional dimension that is smaller than the outer diameter, inner diameter, or other cross-sectional dimension of the proximal and distal regions 20, 24. Each of the regions 20, 22, 24 may have a substantially uniform outer diameter/cross-section along their lengths or, alternatively, may have segments having different diameters/cross-sections. The tubular body 10 includes transitions 21, 23, e.g., isodiametric or other tapered transitions, between the adjacent regions 20, 22, 24.

In an exemplary embodiment, the intermediate region 22 may have a length that is substantially longer than the proximal and distal regions 20, 24. For example, the proximal region 20 may have a length shorter than the handle 30, e.g., such that the entire proximal region 20 may be located within the handle 30, and the distal region 24 may have a length substantially the same as or slightly longer than the deployable and/or expandable device 60 such that the deployable and/or expandable device 60 may be received fully within the distal region 24, e.g., for delivery. The intermediate region 22 may have a length sufficient to introduce the distal region 24 into a location within a patient's body where the deployable device 60 is to be deployed. In exemplary embodiments, the tubular body 10 may have a length between about ten and one hundred thirty centimeters (10-140 cm) between the proximal and distal ends 12, 14. In exemplary embodiments, the distal and proximal regions 24 and 20 may have an outer diameter between six and thirty French and the intermediate region 22 may have an outer diameter between four and twenty-five French.

Figure 2A:
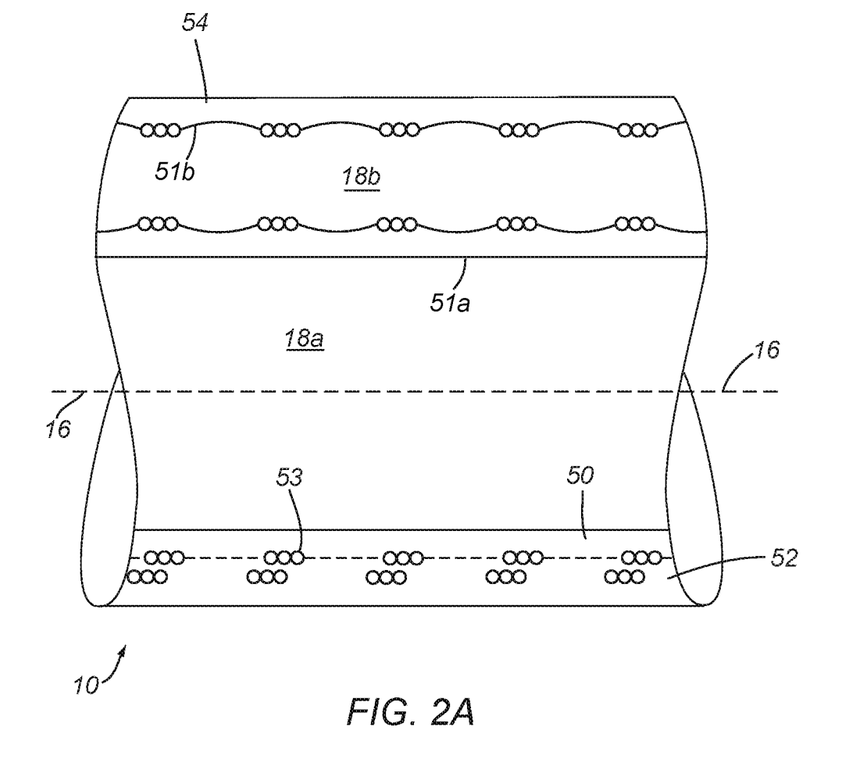
FIG. 2A is a cross-sectional side view of the catheter of FIG. 2, taken along line 2A-2A, showing reinforcement members positioned around a primary lumen and an optional secondary lumen of the catheter.

With particular reference to FIGS. 2 and 2A, the tubular body 10 includes a central or primary lumen 18a, e.g., whose diameter or cross-sectional size varies along the length of the tubular body 10, e.g., within the proximal, intermediate, and distal regions 20, 22, 24, as described further elsewhere herein. For example, in the intermediate region 22, the primary lumen 18a may have a smaller diameter than in the proximal and distal regions 20, 24. In an exemplary embodiment, the primary lumen 18a within the distal region 24 may be sized to receive the deployable and/or expandable device 60, e.g., a stent, stent-graft, cannula, pump, filter, prosthetic valve, and the like, that may be deployed from the primary lumen 18a through an outlet 17 in the distal end 14 and then actuated, released and/or recaptured, or a secondary catheter, electrode, or other device (not shown) that may be deployed from and retracted back into the primary lumen 18a.

In addition, the tubular body 10 may include one or more secondary lumens, e.g., lumen 18b shown in FIG. 2A, extending at least partially between the proximal and distal ends 12, 14 adjacent the primary lumen 18a, e.g., for receiving a steering element, a guide wire, one or more actuation wires, one or more electrical wires or other conductors, one or more optical fibers, one or more tubes or accessory lumens, one or more mechanical elements, one or more sensors (not shown), and/or sized for delivering and/or removing fluids or other flowable agents or materials therethrough.

As best seen in FIG. 2, the handle 30 may surround and/or otherwise encapsulate the proximal region 20 and may be configured and/or sized for holding and/or manipulating the apparatus 8 by a physician or other user, e.g., to direct and/or manipulate the distal end 14 from the proximal end 12. For example, the handle 30 may be permanently attached or otherwise fixed to the tubular body 10, e.g., to secure the proximal region 22 therein, such that the intermediate region 22 extends from the handle 30.

In addition, the handle 30 may include one or more ports, e.g., port 32a communicating with the primary lumen 18a. Optionally, the port 32a may include one or more valves, e.g., a hemostatic valve (not shown), which may provide a substantially fluid-tight seal, while accommodating insertion and/or movement of one or more instruments into/within the primary lumen 18a.

Optionally, the handle 30 may include one or more side ports, e.g., for delivering fluid into the primary lumen 18a and/or one or more secondary lumens (not shown), e.g., through the primary lumen 18a and out the outlet 17. For example, as shown in FIG. 1, a side port 32b may be provided on the handle 30 that communicates with the primary lumen 18a. The side port 32b may include one or more connectors, e.g., a Luer lock connector, for connecting a syringe or other source of fluid (not shown) to the side port 32b such that fluid, e.g., saline, contrast, and the like, may be delivered through the tubular body 10, e.g., around the deployable device 60 and/or into a body lumen within which the distal end 14 is introduced.

As best seen in FIG. 2, a delivery manifold 38 may be slidably disposed relative to the handle 30, e.g., including an inner shaft 42 slidably received through the port 32a and at least partially within the primary lumen 18a. Alternatively, the inner shaft 42 may be otherwise connected to a linkage (e.g., a screw and sled, rack and pinion, lever, etc., not shown) that may cause substantially axial translation of the inner shaft 42 relative to the handle 30 and/or tubular body 10. In an exemplary embodiment, the inner shaft 42 may include a relatively large diameter proximal portion 42a slidably disposed within the proximal region of the primary lumen 18a, and a relatively small diameter distal portion 42b extending through the intermediate region of the primary lumen 18a into the distal region, e.g., such that the deployable and/or expandable device 60 surrounds and/or is otherwise attached to a distal end 42c of the inner shaft 42. The distal end 42c may include an attachment mechanism (not shown) for attaching the deployable and/or expandable device 60 to the distal end 42c.

The proximal portion 42a of the inner shaft 42 may be sized to slide within the proximal portion 20 of the primary lumen 18a with minimal clearance, which may limit movement of the inner shaft 42 relative to the tubular body 20 and/or facilitate using greater force to advance the inner shaft 42, e.g., to deploy the deployable and/or expandable device 60, as described elsewhere herein. The inner shaft 42 may include one or more lumens for carrying fluid and/or elements, e.g. actuators, tensile elements, other devices, etc., including elements connected to or interacting with the deployable and/or expandable device 60. The proximal portion 42a of the inner shaft 42 may be substantially more rigid than the distal portion 42b, for example such that when at least part of the proximal portion 42a is outside of the tubular body 10 substantial axial force may be applied to the proximal portion 42a of the inner shaft inner shaft 42 in order to advance the inner shaft 42 through the tubular body 10 without buckling of the unsupported segment of the proximal portion 42a (i.e. the length outside of the proximal tubular body 10). In an exemplary embodiment, the axial force applied may be between 2 and 50 lbf. The proximal portion 42a may be made more rigid than the distal portion 42b, for example, by addition of embedded stiffening rods or elements, reinforcing elements, e.g. embedded braid elements, addition of tubular element, e.g. one or more hypotubes, tubular elements, laser cut tubular elements, etc. positioned and/or attached to the at least a segment of the proximal portion 42a.

Optionally, the distal portion 42b of the inner shaft 42 may include a relatively large stop 46 proximal to the deployable device 60, e.g., initially within the distal region of the primary lumen 18a, as shown in FIG. 1, which may prevent migration and/or otherwise facilitate deployment of the device 60 when the manifold 38 is moved relative to the tubular body 10, as described elsewhere herein.

Optionally, the manifold 38 may include one or more side ports, e.g., a side port 48 on the hub 44 of the manifold that communicates with a lumen (not shown) that extends through the inner shaft 42 to one or more outlets (also not shown) on the distal end 42c. The side port 48 may include one or more connectors, e.g., a Luer lock connector, for connecting a syringe or other source of fluid (not shown) to the side port 48 such that fluid, e.g., saline, contrast, and the like, may be delivered through the inner shaft lumen into a body lumen within which the distal end 14 is introduced.

The handle 30 may include an actuator 36, e.g., a slider, rotating dial, button, and the like, that may be actuated to direct the manifold 38 from a proximal position, where the distal end 42c of the inner shaft 42 and the deployable device 60 are disposed within the distal region 24 of the tubular body 20, e.g., as shown in FIG. 1, and a distal position, where the deployable device 60 is fully exposed from the distal end 14, e.g., as shown in FIG. 2. In addition or alternatively, the manifold 38 may include a hub 44 on the proximal portion 42a that may be manipulated to direct the inner shaft 42 between the proximal and distal positions by pushing or pulling the hub 44 relative to the handle 30, as described elsewhere herein.

Optionally, the handle 30 and/or manifold 38 may include one or more other actuators, electrical connectors or cables, and the like, for deploying and/or releasing the deployable device 60, activating one or more components on the distal end 14 and/or deployable device 60, and the like. For example, as shown in FIG. 2, an actuator 49 may be provided on the hub 44 that may be manipulated to release the deployable device 60 once deployed and/or otherwise positioned within a target location within the patient's body.

Generally, with particular reference to FIG. 2A, the tubular body 10 may include an inner liner 50, e.g., at least partially or entirely surrounding or otherwise defining the primary lumen 18a, a reinforcement layer 52 surrounding the inner liner 50, and an outer jacket 54 surrounding and/or encasing the reinforcement layer 52, each of which may extend at least partially between the proximal and distal ends 12, 14 of the tubular body 10. The reinforcement layer 52 and/or outer jacket 54 may be attached to the inner liner 50, e.g., by one or more of laminating, adhering, adhesive bonding, ultrasonic welding, reflowing or other heating, and the like, as described elsewhere herein.

In an exemplary embodiment, the inner liner 50 defines an inner surface 51a surrounding the primary lumen 18a. The inner liner 50 may be formed from one or more layers or segments of thermoplastic, fluoropolymer, and/or other polymeric material, optionally, including one or more coatings on the inner surface 51a having desired properties, e.g., a hydrophilic and/or lubricious coating, such as the liners disclosed in U.S. Pat. Nos. 7,550,053, 7,553,387, 8,673,100, and 9,629,978, the disclosures of which are expressly incorporated by reference herein.

Figure 3:
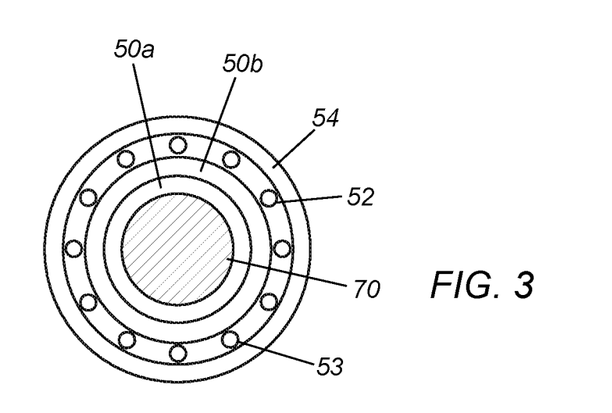
FIG. 3 is a cross-sectional view showing an exemplary catheter layup for making a catheter, such as that shown in FIGS. 1 and 2.

Turning to FIG. 3, an exemplary catheter layup is shown including a mandrel 70, and a series of generally concentric layers, e.g., including an inner layer 50a, an intermediate layer 50b, together defining the inner liner 50, a reinforcing layer 52, and an outer layer 54. In order to achieve desired mechanical, physical, and/or performance properties, each of the layers may be constructed of different materials, which may also be modified along one or more longitudinal segments of the tubular body 10, as desired to provide the desired mechanical properties. Optionally, a liner (not shown) may also at least partially surround the secondary lumen(s) (e.g., lumen 18b in FIG. 2A), which may be formed from one or more layers of material and/or may include one or more coatings on its inner surface 51b, similar to the inner liner 50.

With reference to FIGS. 2A and 3, in one embodiment, the inner layer 50a may be formed from a fluoropolymer, e.g., PTFE, FEP, ETFE, and the like, to provide a lubricious interface for the inner surface 51a, e.g., to facilitate the inner shaft 42 (or other devices) sliding within the primary lumen 18a of the finished catheter 8. Alternatively, the inner layer 50a may include one or more layers of thermoplastic or other polymeric material including one or more coatings on the inner surface having desired properties, e.g., a hydrophilic and/or lubricious coating, e.g., similar to the liners disclosed in the references incorporated by reference herein.

The intermediate layer 50b may be formed from a material capable of adhering to both the inner layer 50a and the reinforcing layer 52 and/or outer layer 54. This may be particularly important when the inner layer 50a is a fluoropolymer and/or other lubricious materials, such as PTFE, FEP, or ETFE, PE, HDPE, and the like, which generally resist bonding to other materials. Optionally, an outer surface of the inner layer 50a may be etched or otherwise treated to enhance bonding to the intermediate layer 50b. More generally, the intermediate layer 50b may be used to bridge any incompatibilities between two or more adjacent layers, be they related to melt-flow, bonding, adherence, chemical, or other properties. Moreover, one or more intermediate layers may be used for other purposes, such as providing insulation (e.g., electrical, thermal, chemical, etc.), for modulating mechanical properties, for isolation of material from direct body contact, as a reservoir for drugs or other substances, e.g., to facilitate elution over time, and/or to increase tensile strength, burst pressure, or otherwise improve mechanical characteristics.

With continued reference to FIGS. 2A and 3, the reinforcement layer 52 may include one or more reinforcing members 53, e.g., wound in a coil, braided, or other helical configuration around the one or more layers of the inner liner 50, e.g., manually or using a braiding apparatus, such as those shown in U.S. Pat. Nos. 9,427,551 and 10,065,015, the entire disclosures of which are expressly incorporated by reference herein. In exemplary embodiments, the reinforcement layer 52 may include a plurality of round or flat (e.g., rectangular, elliptical, or flat oval) wires, filaments, strands, or other reinforcement members 53, e.g., formed from metal, such as stainless steel, plastic, such as PEEK, glass, woven or twisted fibers, such as aramid, and the like, or composite materials.

In one embodiment, a plurality of reinforcement members 53 may be braided around the inner liner 50 (after applying the one or more layers defining the liner 50 around a mandrel, such as mandrel 70 shown in FIG. 3), e.g., with each reinforcement member 53 having the same material and/or shape. Alternatively, the reinforcement members 53 may have different sizes, materials, and/or shapes, e.g., a first size or shape extending helically in a first direction and a second size or shape (different than the first) extending helically in a second direction (e.g., opposite the first direction).

The reinforcement layer 52 may be configured to substantially transfer torsional forces between the proximal and distal ends 12, 14, e.g., to allow the tubular body 10 to be twisted from the proximal end 12 to rotate the distal end 14 about the longitudinal axis 16 within a patient's body. In addition, the reinforcement layer 52 may allow the distal end 14 of the tubular body 10 to be advanced or otherwise manipulated within a patient's body from the proximal end 12 without substantial risk of buckling and/or kinking. Optionally, the pitch of the reinforcement layer 42 may be varied along the length of the tubular body 10, e.g., in order to optimize mechanical properties of various segments or portions of the tubular body 10, e.g., as described elsewhere herein or in the references incorporated by reference herein.

In addition, the location of the reinforcement layer 52 may vary relative to the primary lumen 18a and/or any secondary lumens (such as lumen 18b shown in FIG. 2A), e.g., as the secondary lumen(s) transition to different radial locations within the wall of the tubular body 10, as described in the references incorporated by reference herein.

The outer jacket 54 may include one or more tubular, rolled, or extruded layers surrounding the reinforcement layer 52 and/or between the reinforcement layer 52 and the inner liner 50. In an exemplary embodiment, the outer jacket 54 may be formed from one or more layers of PEBAX, nylon, urethane, and/or other thermoplastic material, e.g., such that the material of the outer jacket 54 may be heated and reflowed and/or otherwise formed around the reinforcement layer 52 and liner 50, e.g., as described elsewhere herein.

In one embodiment, one or more of the layers of the tubular body 10 may have a substantially homogenous construction between the proximal and distal ends 12, 14. Alternatively, the construction may vary along the length of the tubular body 10 to provide desired properties, e.g., between the proximal, intermediate, and distal regions 20, 22, 24. For example, the proximal region 20 may be substantially rigid or semi-rigid, e.g., providing sufficient column strength to allow the distal end 14 of the tubular body 10 to be pushed or otherwise manipulated from the proximal end 12, while the distal region 24 may be substantially flexible.

Figure 4A:
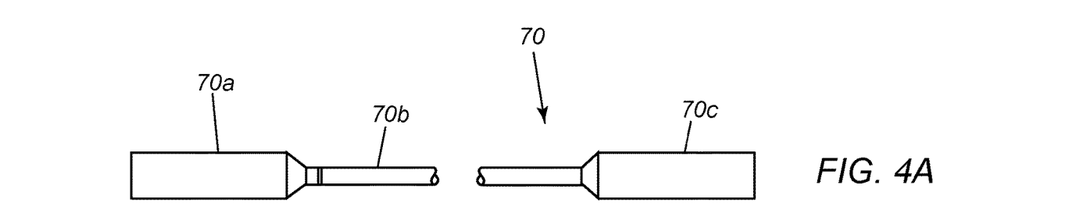
FIGS. 4A and 4B are side views of an example of a two-part mandrel that may be used in a method for making the catheter of FIGS. 1 and 2.

Turning to FIG. 4A, with continued reference to FIG. 3, an exemplary method for making a tubular body 10 generally includes providing a mandrel 70 including a proximal segment 70a having a first diameter, an intermediate segment 70b extending from the proximal segment having a second diameter, and a distal segment 70c having a third diameter extending from the intermediate segment 70b opposite the proximal segment 70a. As shown in FIG. 4A, the diameter of the intermediate segment 70b is smaller than the diameter of the proximal and distal segments 70a, 70c, e.g., corresponding to the desired inner diameter of the primary lumen 18a within different regions of the tubular body 10. In addition, the length of the intermediate segment 70b may be substantially longer than the length of the proximal and distal segments 70a, 70c.

Initially, a liner may be applied around the mandrel 70, e.g., entirely or partially between the distal and proximal segments 70c, 70b. For example, as shown in FIG. 3, a first or inner layer 50a of material may be applied around the mandrel 70 and then a second or intermediate layer 50b may be applied around the mandrel 70 over the inner layer 50a. In an exemplary embodiment, the inner layer 50a may be formed as a tubular sleeve, e.g., of heat shrink or other material, such as those described elsewhere herein, initially having a diameter larger than the proximal and distal segments 70a, 70c that may be positioned around the mandrel 70 and then heated or otherwise activated to reduce the diameter of the sleeve such that the sleeve fits snugly around the mandrel 70. A single sleeve may extend entire over the mandrel 70, i.e., over the proximal, intermediate, and distal regions 70a-70c, or, alternatively, multiple sleeves having desired properties may be inserted over different regions of the mandrel 70 and heated such that each of them fit snugly over the mandrel 70. In this alternative, edges of adjacent sleeves may be disposed adjacent, e.g., butted against, one another or may partially overlap one another (not shown).

Figure 6A:
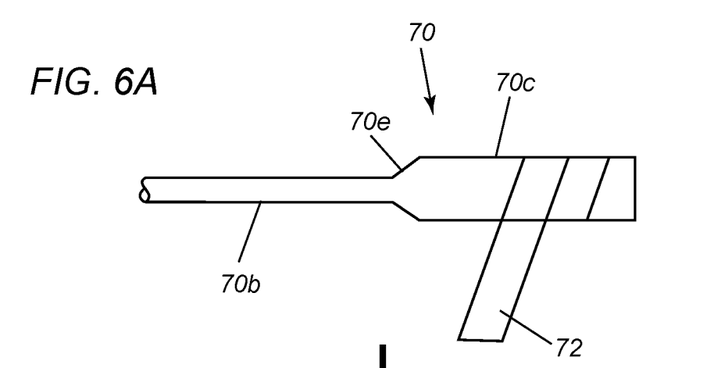
FIGS. 6A and 6B are side views of a mandrel showing a layer of liner material being applied helically from a distal region over a transition to an intermediate region of the mandrel.
Figure 6B:
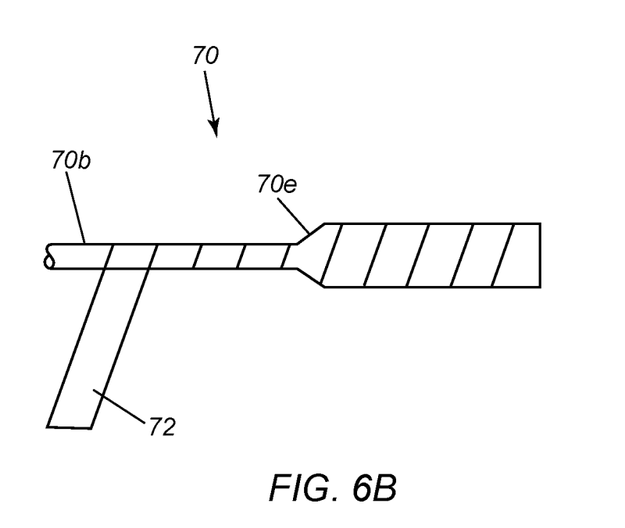

Once the inner layer 50a is applied, a second or intermediate layer 50b may be applied around the mandrel 70 over the inner layer 50a. For example, as shown in FIGS. 6A and 6B, a long strip of material 72 may be wound helically around the mandrel 70, e.g., from the distal end 70c (or alternatively from the proximal end 70a) at least partially over the intermediate layer 70b. In one embodiment, the strip 72 may be wound over the entire length of the mandrel 70 (initially from the distal segment 70c or the proximal segment 70a), or multiple strips having different properties may be wound over different regions of the mandrel 70, as desired. One advantage of helically winding the strip 72 is that the helical angle may be changed as desired, e.g., to facilitate wrapping the strip 72 around a transition 70e between the distal and intermediate regions 70b, 70c (and similarly over a transition, not shown, between the proximal and intermediate regions 70a, 70b) with a relatively tight fit that minimizes gaps around the mandrel 70.

Figure 7:
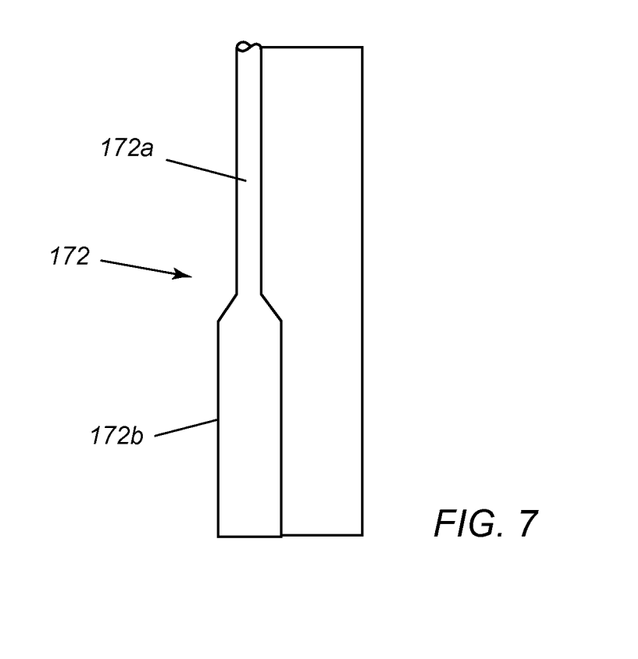
FIG. 7 is side view of a strip having a variable thickness, i.e., a first relatively thin region and a second relatively thick region.

In an alternative embodiment, the inner layer 50a may be created by wrapping one or more strips of material helically around the mandrel 70, whereupon the intermediate layer 50b may also be wrapped helically or may be omitted. In another alternative, one or more strips having variable thickness along their length may be used. For example, as shown in FIG. 7, a strip 172 may be provided having a relatively thin first region 172a along a first length and a relatively thicker region 172b having a second length. Optionally, multiple different thickness regions may be provided as desired, e.g., corresponding to transitions on a mandrel around which the strip is wrapped.

Figure 8:
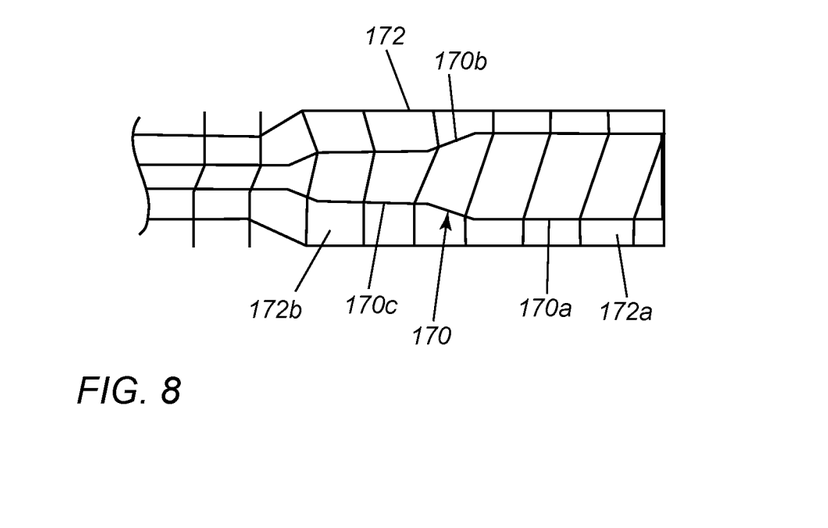
FIG. 8 is a cross-sectional view of a mandrel having stepped regions, showing a variable thickness strip, such as that shown in FIG. 7, wrapped around the mandrel to fit snugly around the stepped regions while provide a substantially uniform outer diameter.

For example, as shown in FIG. 8, a mandrel 170 is shown having a first segment 170a having a first diameter, a first transition 170b tapering to a second segment 170c having a second, smaller diameter (and optionally having one or more transitions). A strip 172 may be wrapped around the mandrel 170, initially wrapping a relatively thin around the first segment 170a with the first, relatively thin region 172a. The length of the first region 172a may be set such that the second thicker region 172b wraps around the transition 170b and the second segment 170c, thereby providing a substantially uniform outer diameter. Thus, different thickness strips may be used over a variable diameter mandrel, e.g., to provide an inner lumen for a finished tubular device having a variable diameter based on the mandrel 170, while providing one or more uniform outer diameter regions.

Returning to FIG. 3, after creating the wrapped inner liner 50/mandrel 70 assembly, a reinforcement layer 52 may be directed around the layer(s) of the liner 50, e.g., by braiding a plurality of reinforcement members 53 around the assembly to secure the liner 50 around the mandrel 70. The reinforcement layer 52 may be applied by feeding the assembly through an automatic braiding apparatus (not shown), such as those described in the references incorporated by reference herein, or manually. Optionally, if the finished tubular body includes one or more secondary mandrels, secondary mandrels (not shown) may be positioned adjacent the assembly, e.g., such that the second mandrels are captured by the reinforcement members 53, for example, braided into or entirely surrounded by the reinforcement members 53.

An outer jacket 54 may then be directed over the reinforcement layer/liner/mandrel assembly, e.g., automatically by feeding the assembly through a jacket applying apparatus, e.g., to extrude jacket material over the assembly, by inserting one or more tubular segments over the assembly, and/or wrapping one or more sheets of material around the assembly (not shown), thereby providing a layup assembly shown in FIG. 3.

The layup assembly of FIG. 3 may be heated, reflowed, laminated, and/or bonded to create a composite tubular structure around the mandrel 70. The mandrel 70 may then be removed to provide a tubular body 10, such as that shown in FIGS. 1 and 2, defining a proximal region 20 corresponding to the proximal segment 70a, an intermediate region 22 corresponding to the intermediate segment 70b, and a distal region 24 corresponding to the distal segment 70c of the mandrel 70.

Figure 4B:
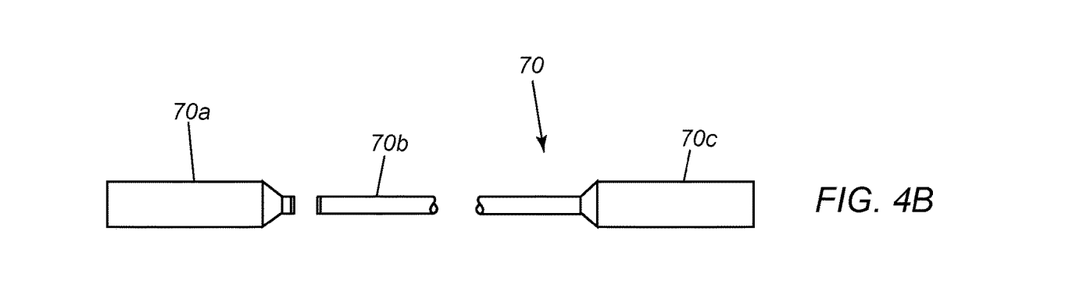

In the embodiment shown in FIGS. 4A and 4B, the mandrel 70 may be formed as two pieces, e.g., a first piece including the proximal segment 70a and a second piece including the intermediate and distal segments 70b, 70c. The pieces may be removably secured together using one or more cooperating connectors (not shown), such as mating threads, an interference fit, and the like. Thus, once the tubular body 10 has been created, the first piece may be disconnected from the second piece (e.g., by rotating to unthread the connectors, pulling to overcome the interference fit, and the like), to remove the proximal segment 70a from the proximal portion 20 of the tubular body 10. The second piece may then be pulled from the distal end 14 to remove the intermediate and distal segments 70b, 70c from the intermediate and distal regions 22, 24.

Figure 5A:
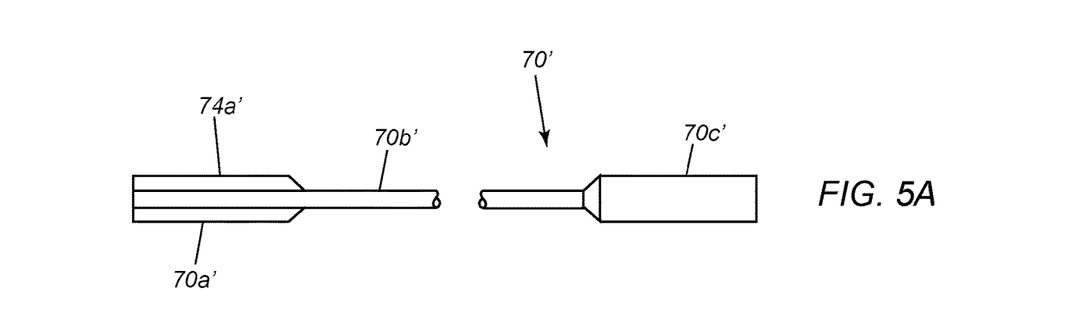
FIGS. 5A and 5B are side views of another example of a two-part mandrel that may be used in a method for making the catheter of FIGS. 1 and 2.
Figure 5B:
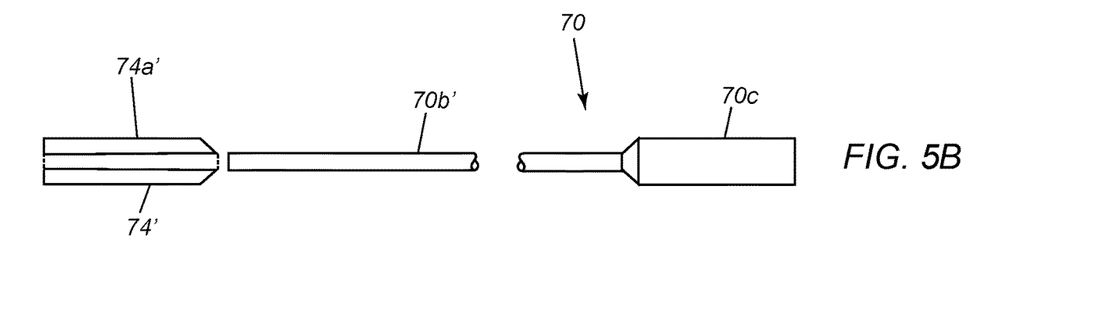

Alternatively, as shown in FIGS. 5A and 5B, a mandrel 70' is shown that includes a single piece that includes a distal segment 70c', an intermediate segment 70b' having a smaller diameter than the distal segment 70c', and a proximal segment 70a' having the same diameter as the intermediate segment 70b'. In this alternative, an annular shim 74' may be provided over the proximal segment 70a' that has a length corresponding to the desired length of the proximal region 20 of the finished tubular body 10. The shim 74' may include a taper 74a' corresponding to a transition between the proximal and intermediate regions 20, 22 of the tubular body 10. Optionally, multiple concentric shims (not shown) may be provided over the proximal segment 70a', if desired, to provide the desired inner diameter of the primary lumen 18a within the proximal region 20.

Thus, in this alternative, after creating the tubular member, the shim 74' may be removed from the proximal segment 70a', e.g., by simply pulling the shim 74' out from within the proximal region 20. The entire mandrel 70' may then be removed from within the tubular body 10 from the distal region 24.

If any secondary mandrels are included when creating the tubular body 10, the secondary mandrels may be removed before or after the mandrel 70, 70'. The resulting tubular body 10 may then be incorporated into a catheter or other apparatus, such as the apparatus 8 shown in FIGS. 1 and 2.

For example, with reference to FIGS. 1 and 2, a handle 30 may be formed, e.g., by molding, casting, and the like, and attached to the proximal end 12 of the tubular body 10, e.g., such that the entire proximal region 20 of the tubular body 10 is captured within the handle cavity.

The manifold 38, e.g., inner shaft 42 and hub 44, may be formed and inserted into the port 32a of the handle 30 to position the distal end 42c of the inner shaft 42 within the distal region 24 of the tubular body 10, and the deployable device 60 may be positioned in the distal region 24 over the distal end 42c. For example, the manifold 388 may be advanced until the distal end 42c is disposed outside the distal region 24, e.g., similar to the position shown in FIG. 2, and the deployable device 60 may be mounted on the distal end 42c, whereupon the manifold 38 may be retracted to direct the deployable device 60 into the distal region 24 of the primary lumen 18a.

For example, if the deployable device 60 were an expandable prosthesis, e.g., a stent, stent-graft, or valve prosthesis (not shown), the prosthesis 60 may be compressed to a reduced profile sized to be received within the distal region 24. In one embodiment, the prosthesis 60 may be positioned within the distal region 24 such that, upon deployment from the distal region 24, the prosthesis 60 automatically expands to an expanded profile. Alternatively, one or more constraints (not shown) may be provided that maintain the prosthesis 60 in the reduced profile, e.g., during loading, and introduction into a patient's body, that may be directed through one or more secondary lumens (also not shown) of the tubular body 10. The constraints may be coupled to an actuator on the handle 30 or hub 38 such that, when the prosthesis 60 is deployed from the distal region 24, the prosthesis 60 may remain in the reduced profile until the actuator is activated to release or remove the constraints.

Any other desired components may be added to the tubular body 10, handle 30, and/or manifold 38 to provide the finished apparatus 8. Once the final apparatus 8 is assembled, the apparatus 8 may be sterilized and/or otherwise processed and packaged. The apparatus 8 may then be provided to a physician or other user to perform a medical procedure within a patient's body.

During use, the apparatus 8 may be introduced into a patient's body to perform a medical procedure. For example, the distal region 24 with the deployable device 60 therein, may be introduced via a percutaneous puncture, e.g., over a guidewire and/or through an introducer sheath (not shown), into the patient's vasculature, and advanced to a target location. Once positioned as desired, the deployable device 60 may be deployed from the distal region 24, e.g., by manipulating the actuator 36 to advance the inner shaft 42 relative to the tubular body 10, thereby directing the distal end 42c of the inner shaft 42 and the device 60 thereon from the outlet 17, e.g., as shown in FIG. 2. Alternatively, the handle 30 may be retracted relative to the hub 44 (or the hub 44 advanced relative to the handle 30) to deploy the device 60.

The relatively large proximal portion 42a of the inner shaft 42 may slide within the relatively large diameter region of the primary lumen 18a within the proximal region 20 with minimal clearance. Given the relatively larger diameter of the proximal portion 42a, greater forces may be applied, if desired, to advance the inner shaft 42 and deploy the device 60. In addition, the stop 46 may prevent migration of the device 60, i.e., ensure that the device 60 remains on the inner shaft distal end 42c as the inner shaft 42 is advanced.

In one embodiment, where the device 60 is a prosthesis intended for implantation within the target location, e.g., a stenosis, a native valve site, and the like, the actuator 49 on the hub 44 may be manipulated to release the device 60 within the target location. For example, if the actuator 49 is coupled to one or more constraints (not shown) around the device 60, the actuator 49 may be used to release them. Alternatively, the actuator 49 may disconnect one or more connectors (also not shown) coupling the device 60 to the inner shaft 42, thereby releasing the device 60. Once the device is deployed and released, the apparatus 8 may be removed using conventional methods.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a tubular device including relatively large proximal and distal ends, comprising:
   providing a mandrel including a proximal segment having a first diameter, an intermediate segment extending from the proximal segment having a second diameter, and a distal segment having a third diameter extending from the intermediate segment opposite the proximal segment, the second diameter being smaller than the first and third diameters, wherein the proximal segment comprises an inner portion having a diameter corresponding to the second diameter and a shim surrounding the inner portion defining the second diameter;
   applying a liner around the mandrel between the distal, intermediate, and proximal segments;
   directing a reinforcement layer around the liner over at least a portion of the mandrel;
   directing an outer jacket over the reinforcement layer and the liner between the distal, intermediate, and proximal segments; and
   removing the mandrel to provide a tubular body comprising a primary lumen defining a proximal region corresponding to the proximal segment, an intermediate region corresponding to the intermediate segment, and a distal region corresponding to the distal segment of the mandrel,
   wherein removing the mandrel comprises:
   removing the shim around the inner portion from the tubular body proximally from the proximal region; and
   removing the inner portion, intermediate segment, and distal segment of the mandrel together from the tubular body distally from the distal region; wherein the shim comprises a taper providing a transition from the proximal segment to the intermediate segment.

2. The method of claim 1, wherein the primary lumen has a proximal diameter within the proximal region, an intermediate diameter within the intermediate region, and a distal diameter within the distal region, the intermediate diameter being smaller than the proximal and distal diameters.

3. The method of claim 1, wherein applying the liner comprises wrapping liner material helically around the mandrel from the distal segment to the intermediate segment.

4. The method of claim 3, wherein the mandrel comprises a distal transition from the distal segment to the intermediate segment, and wherein wrapping liner material around the mandrel comprises wrapping the liner material around the distal transition, thereby changing a helical angle of the liner material to maintain a tight fit around the mandrel between the distal and intermediate segments.

5. A method for making a tubular device including relatively large proximal and distal ends, comprising:
providing a mandrel including a proximal segment having a first diameter, an intermediate segment extending from the proximal segment having a second diameter, and a distal segment having a third diameter extending from the intermediate segment opposite the proximal segment, the second diameter being smaller than the first and third diameters;
applying a liner around the mandrel between the distal, intermediate, and proximal segments;
directing a reinforcement layer around the liner over at least a portion of the mandrel;
directing an outer jacket over the reinforcement layer and the liner between the distal, intermediate, and proximal segments; and
removing the mandrel to provide a tubular body comprising a primary lumen defining a proximal region corresponding to the proximal segment, an intermediate region corresponding to the intermediate segment, and a distal region corresponding to the distal segment of the mandrel,
applying the liner comprises wrapping liner material helically around the mandrel from the distal segment to the intermediate segment
wherein the mandrel comprises a distal transition from the distal segment to the intermediate segment, and wherein wrapping liner material around the mandrel comprises wrapping the liner material around the distal transition, thereby changing a helical angle of the liner material to maintain a tight fit around the mandrel between the distal and intermediate segments, and
wherein the liner material comprises a strip of material having a first region having a first thickness and a second region having a second thickness greater than the first thickness, and wherein the first region of the strip is wrapped around the distal segment, and the second region of the strip is wrapped around the transition and at least partially along the intermediate segment such that the liner has a substantially uniform outer diameter around the distal segment, the transition, and at least a portion of the intermediate segment.

6. The method of claim 1, wherein applying the liner comprises:
inserting a tubular liner over the mandrel that extends between the proximal and distal segments; and
applying a helical liner over the tubular liner by wrapping liner material helically around the mandrel from the distal segment at least to the intermediate segment.

7. The method of claim 6, wherein the tubular liner comprises heat shrink material, and wherein applying a liner further comprises applying heat to the tubular liner to cause the tubular liner to shrink and fit tightly around the mandrel between the proximal and distal segments.

8. The method of claim 6, wherein the tubular liner comprises a material providing a lubricious inner surface for the primary lumen.

9. The method of claim 8, wherein the material of the tubular liner is a fluoropolymer.

10. The method of claim 9, wherein the helical liner comprises a thermoplastic material.

11. The method of claim 1, further comprising:
positioning a secondary mandrel adjacent the primary mandrel before directing the reinforcement layer around the liner such that one or more reinforcement members of the reinforcement layer overlie the secondary mandrel; and
removing the secondary mandrel after directing the outer jacket over the reinforcement layer, thereby creating a secondary lumen.

12. The method of claim 1, further comprising attaching a handle or hub at least partially over the proximal region of the tubular body.

13. A method for making a tubular device including relatively large proximal and distal ends, comprising:
providing a mandrel including a distal segment having a first diameter, a second segment extending from the distal segment having a second diameter smaller than the first diameter, and a transition therebetween tapering from the first diameter to the second diameter;
providing a shim surrounding a portion of the second segment spaced apart from the distal segment such that the shim defines a proximal segment having a third diameter and the second segment between the proximal and distal segments defines an intermediate segment having the second diameter;
applying a liner around the mandrel between the distal, intermediate, and proximal segments;
directing a reinforcement layer around the liner over at least a portion of the mandrel;
directing an outer jacket over the reinforcement layer and the liner between the distal, intermediate, and proximal segments; and
removing the shim around the portion of the second segment from a tubular body proximally from a proximal region; and
removing the distal segment, the intermediate segment, and the second segment of the mandrel together from a tubular body distally from a distal region to provide the tubular body comprising a primary lumen defining the proximal region corresponding to the proximal segment, the intermediate region corresponding to the intermediate segment, and the distal region corresponding to the distal segment of the mandrel; wherein the shim comprises a taper providing a transition from the proximal segment to the intermediate segment.

14. The method of claim 13, wherein the shim comprises a first annular shim provided around the inner segment of the mandrel.

15. The method of claim 13, wherein the shim comprises a plurality of concentric shims provided over the inner segment to define a desired third diameter for the proximal segment.

16. The method of claim 1, wherein applying the liner comprises wrapping a strip around a transition between the distal and intermediate segments and over a transition between the proximal and intermediate segments with a tight fit that minimizes gaps around the mandrel.

17. The method of claim 1, wherein the mandrel comprises a transition therebetween tapering from the third diameter to the second diameter.

* * * * *